US009248095B2

(12) United States Patent
Chang et al.

(10) Patent No.: US 9,248,095 B2
(45) Date of Patent: Feb. 2, 2016

(54) NUTRITIONAL SUPPLEMENT SYSTEM

(71) Applicant: Shaklee Corporation, Pleasanton, CA (US)

(72) Inventors: Kuei-tu Chang, San Jose, CA (US); Carsten R. Smidt, Sandy, UT (US); John Castillo, Newark, CA (US); William J. Mergens, West Palm Beach, FL (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

(21) Appl. No.: 14/194,528

(22) Filed: Feb. 28, 2014

(65) Prior Publication Data

US 2014/0178347 A1    Jun. 26, 2014

Related U.S. Application Data

(63) Continuation of application No. 12/699,798, filed on Feb. 3, 2010, now abandoned, which is a continuation of application No. PCT/US2008/009399, filed on Aug. 4, 2008, and a continuation-in-part of application No. PCT/US2008/009402, filed on Aug. 4, 2008.

(60) Provisional application No. 60/953,934, filed on Aug. 3, 2007, provisional application No. 60/953,944, filed on Aug. 3, 2007.

(51) Int. Cl.

| A23L 1/29 | (2006.01) |
|---|---|
| A61K 9/00 | (2006.01) |
| A23L 1/30 | (2006.01) |
| A23L 1/302 | (2006.01) |
| A23L 1/304 | (2006.01) |
| A61K 9/24 | (2006.01) |
| A61K 9/28 | (2006.01) |
| A61K 9/48 | (2006.01) |

(52) U.S. Cl.
CPC ............. *A61K 9/0053* (2013.01); *A23L 1/3002* (2013.01); *A23L 1/302* (2013.01); *A23L 1/304* (2013.01); *A23L 1/3008* (2013.01); *A23V 2002/00* (2013.01); *A61K 9/209* (2013.01); *A61K 9/286* (2013.01); *A61K 9/2866* (2013.01); *A61K 9/4866* (2013.01); *A61K 9/4891* (2013.01)

(58) Field of Classification Search
CPC ... A61K 9/006; A61K 9/4891; A61K 9/5084; A23L 1/304; A23L 1/302; A23V 2200/08
USPC ...................... 426/72, 73, 74, 658, 2, 89, 454
See application file for complete search history.

(56) References Cited

U.S. PATENT DOCUMENTS

| 3,870,790 A | 3/1975 | Lowey et al. |
|---|---|---|
| 4,389,393 A | 6/1983 | Schor et al. |
| 5,445,826 A | 8/1995 | Kuhrts |
| 5,494,678 A | 2/1996 | Paradissis et al. |
| 5,723,446 A | 3/1998 | Gray et al. |
| 5,843,887 A | 12/1998 | Petit et al. |
| 6,451,341 B1 | 9/2002 | Slaga et al. |
| 6,805,880 B1 | 10/2004 | Højgaard et al. |
| 2003/0148992 A1 | 8/2003 | Block et al. |
| 2004/0091537 A1* | 5/2004 | Miller ........................... 424/471 |
| 2004/0142036 A1 | 7/2004 | Abrams et al. |
| 2006/0251722 A1 | 11/2006 | Bandak et al. |
| 2006/0270625 A1 | 11/2006 | Vinik et al. |

FOREIGN PATENT DOCUMENTS

| EP | 208362 A1 | 1/1987 |
|---|---|---|
| EP | 327086 A2 | 8/1989 |
| JP | H05505935 A | 9/1993 |
| WO | WO 91/1117 A2 | 8/1991 |
| WO | WO 00/07463 A1 | 2/2000 |
| WO | WO 01/72286 A1 | 10/2001 |
| WO | WO 2004/052295 A2 | 6/2004 |
| WO | WO 2005/079853 A2 | 9/2005 |
| WO | WO 2006/054135 A1 | 5/2006 |

OTHER PUBLICATIONS

Bockus, *Gastroenterology* 2:947-948 (1995).
International Search Report and Written Opinion, mailed Feb. 4, 2009, in corresponding International Application No. PCT/US2008/009399.
Office Action, dated Apr. 23, 2013, issued in JP Application No. 2010-519969.
Examination and Search Report, dated Jun. 3, 2013, issued in Taiwan Application No. 097129487.

* cited by examiner

*Primary Examiner* — Helen F Heggestad
(74) *Attorney, Agent, or Firm* — Klarquist Sparkman, LLP

(57) ABSTRACT

A multi-part nutritional supplement system supplies nutrients to a user at advantageous locations in the digestive tract. One type of dosage unit is formulated to release vitamin B12 in the stomach and intestines of the upper GI tract, advantageously in an amount that is greater than or at multiple levels of the DV (Daily Value) of vitamin B12.

21 Claims, No Drawings

NUTRITIONAL SUPPLEMENT SYSTEM

CROSS REFERENCE TO RELATED APPLICATIONS

This is a continuation of application Ser. No. 12/699,798, filed Feb. 3, 2010, which is a continuation of International Application No. PCT/US2008/009399, filed Aug. 4, 2008, which claims the benefit of U.S. Provisional Application No. 60/953,934, filed Aug. 3, 2007 and U.S. Provisional Application No. 60/953,944, filed Aug. 3, 2007.

This is a continuation of application Ser. No. 12/699,798, filed Feb. 3, 2010, which is a continuation-in-part of International Application No. PCT/US2008/009402, filed Aug. 4, 2008, which claims the benefit of U.S. Provisional Application No. 60/953,934, filed Aug. 3, 2007 and U.S. Provisional Application No. 60/953,944, filed Aug. 3, 2007.

All the above-referenced applications are incorporated herein by reference.

BACKGROUND AND SUMMARY

Described herein is a nutritional supplement system for the delivery of vitamins, minerals, and/or probiotics for sustaining the health of human subjects.

Vitamin and mineral preparations are commonly administered as general nutritional supplements. Micronutrients are elements or compounds which are present in foods and herbs in small or trace amounts. These include vitamins, minerals, or other elements, and substances found in foods. The macronutrients consist of carbohydrates, fats, and proteins, which supply nutrients and calories. Some elements such as calcium, sodium, potassium, chloride, and phosphorus are consumed in relatively large amounts, while many such as iron, iodine, and zinc are consumed in small amounts. Vitamins, such as vitamin B12 and folic acid, and the minerals copper, selenium, and chromium are consumed in very small or trace amounts.

Inasmuch as the human body does not synthesize many compounds which are essential to the human body, certain vitamins, minerals, and other nutrients can be obtained from only two sources, food and supplements. The primary source of all nutrients is food. However, many people do not acquire optimal amounts of the essential compounds and elements from the foods they eat. Thus, nutritional supplementation has become a recognized method of preserving good health.

The consumption of probiotic supplements also can be beneficial to the well being of humans. It has been recognized that temporary or chronic digestive symptoms can be caused by a damaged or disordered intestinal flora. Consumption of a nutritional supplement preparation containing suitable microorganisms is often sufficient to alleviate or to eliminate the symptoms caused by a disordered or damaged intestinal flora.

As used herein, "probiotics" refers to live micro-organisms, delivered in food supplements, which beneficially affect the host animal by improving its intestinal microbial balance. Antibiotics and other related compounds are not included in this definition. (*J. Nutr.* 1995; 125:1401-12). For humans, lactobacilli are commonly provided as probiotics, either as single species or in mixed culture with other bacteria. Other genera that have been used are bifidobacteria and streptococci. "Prebiotics" refers to non-digestible food ingredients that beneficially affect the host by selectively stimulating the growth and/or activity of bacteria in the colon.

It has been a problem with many prior nutritional supplement systems that they provide incomplete nutrition or that a multiplicity of doses of nutrients must be taken at multiple different times to achieve a well balanced and appropriately timed delivery of nutrients to a user. Prior nutritional supplement systems have in some cases delivered nutrients to a location in the digestive tract where, although effective for uptake of the nutrients, have caused user discomfort. In other cases, one or more nutrients are released in a location that is not optimal for uptake by the body. When nutrients or probiotics are released in locations that are unfavorable reduce biological activity can result. For example, probiotics typically do not survive exposure to stomach acid.

It has been a specific problem in the formulation of supplements for the delivery of vitamin B12 that the absorption of vitamin B12 has been found to require secretion of a glycoprotein, known as "intrinsic factor," from cells lining the stomach. Normally, vitamin B12 is readily absorbed in the last part of the small intestine (ileum), which leads to the large intestine. However, to be absorbed, the vitamin must combine with intrinsic factor. As a result of passage through the stomach, vitamin B12 is attaches to intrinsic factor for transfer. This combination of the vitamin and intrinsic factor can then be "caught" by the ileal receptor. Without intrinsic factor, significant amounts of vitamin B12 can remain in the intestine and are excreted in the stool. Previously it has been thought that, to maximize the absorption of vitamin B12, a supplement should be formulated to deliver vitamin B12 in the stomach to maximize binding to intrinsic factor and optimize uptake of the intrinsic factor/B12 complex. But there are difficulties with supplements that provide for rapid release vitamin B12 in the stomach.

There thus is a continuing need for user friendly systems for effectively delivering beneficial substances to the body.

In answer to that need a nutritional supplement system is provided that supplies nutrients and/or probiotics at various appropriate locations in the digestive tract.

One particular element of such a system is a dosage unit formulated to release vitamin B12 over time in both the stomach and the intestines of the upper GI tract.

DETAILED DESCRIPTION

A multi-component oral nutritional supplement system supplies a combination of nutrients and/or probiotics at optimal locations throughout the digestive tract of a human subject for efficient nutrient utilization and user comfort and convenience.

An optimal system includes four dosage units, although certain other beneficial systems may include two or three dosage units.

A first dosage unit that is formulated to quickly release one or more nutrients in the stomach of a human subject. This dosage unit advantageously includes vitamins and minerals or other dietary supplement ingredients that benefit from release in the stomach and exposure to stomach acid, or are not adversely affected by such release or exposure, and/or properly are dispersed in the stomach for optimal absorption further down in the GI tract. This dosage unit advantageously is in the form of a tablet or caplet formed by compression. The tablet may be coated with a layer containing one or more nutrients that best are delivered in the stomach particularly rapidly. In general, the first dosage unit should not contain substances that are not well tolerated by the stomach or that would be harmed by the acidic environment of the stomach; such substances should be delivered in one of the other dosage units described herein.

A second dosage unit is formulated to contain nutrients that do not require release in the stomach and exposure to stomach acid for efficient digestion and absorption, and which may cause tolerance problems (repeating, stomach upset, nausea) or loss in biological activity when released in the stomach. This dosage unit advantageously is used to deliver certain nutritional oils, notably fish oil constituents, other omega-3 fatty acid containing oils, and may also include fat-soluble micronutrients that do not require stomach digestion, such as vitamins A, D, E, and carotenoids. The dosage unit advantageously is a sealed gelatin encapsulation that can pass through the stomach before releasing the encapsulated nutrients.

A third dosage unit is formulated to contain water-soluble nutrients and other nutrients that are typically very rapidly absorbed and therefore best delivered by sustained release so as to maintain an elevated concentration in the body over time. This dosage unit is designed to slowly, in generally linear fashion, release one or more water-soluble nutrients. The release of these nutrients is initially in the stomach and continues into the intestines of the upper GI tract. This dosage unit advantageously is formulated to release vitamin B12. The dosage unit also is useful to deliver other B-vitamins and vitamin C.

A fourth dosage unit contains nutrients and/or other supplement ingredients such as probiotics that are adversely affected by exposure to stomach acid or stomach digestion, and that should be delivered into the lower parts of the small intestine for full activity in the large intestine. This dosage unit is formulated to protect the probiotic microorganisms from potentially lethal acid exposure during passage of the dosage unit through the stomach. Advantageously it is in the form of a three-layer capsule.

These four dosage units are formulated for administration one time each day, and can be taken substantially simultaneously, to provide complete and appropriately timed delivery of a full range of nutrients and probiotics.

All the dosage units of complete daily dose of the nutritional supplement system advantageously are packaged together as a multi-element package so that a user will not need to remember to combine various individual dosage units to make a complete daily dose. In some cases, to avoid the use of uncomfortably large tablets, caplets, or capsules, certain of the dosage units can be split into two or more tablets, caplets, or capsules. Because a balanced supplement system requires relatively large amount of the nutrients of the first and second dosage units, in a particularly advantageous arrangement the first dosage unit is in the form of two separate dosage elements, preferably tablets or caplets, and the second dosage unit is in the form of two separate dosage elements, preferably gel encapsulations. With that arrangement, the two first dosage unit elements, the two second dosage unit elements, one third dosage unit element, and one fourth dosage unit element can be provided together, for example in a single blister pack card or strip, so that a user will immediately know that the six elements together are a day's dose. A typical blister pack arrangement will have six attached blister strips, separated by perforated detachment lines, with each strip holding the six dosage elements that together comprise a day's dose.

The dosage units advantageously employ various forms of extended release excipients or coatings along with immediate release excipients or coatings to deliver the various vitamins and mineral supplements over various optimum rates of release. For example, a folic acid micro-coating can be employed to release folic acid from the multi-vitamin and mineral supplement within minutes after entry into the stomach. Gel diffusion technology can be used to maximize the intestinal adsorption of vitamins B and C for over twelve hours. Providing fish oil in delayed release capsules results in rapid release in the intestines of upper GI tract, which gives maximum bioavailability and minimum stomach discomfort. And a triple layer encapsulation system provides for targeted release of probiotics to the lower GI tract.

In general, those of ordinary skill know how to formulate dosage units with various different release profiles. Nutritional supplement dosage units may employ one or more forms of release, including, without limitation, immediate release, extended release, pulse release, variable release, controlled release, timed release, sustained release, delayed release, long acting, and combinations thereon. The various types of release can be accomplished using well known procedures and techniques.

The time release characteristics for the release of the components may be varied by modifying the composition of layers, including modifying any of the excipients or coatings which may be present. For example, changing the composition or amount of the covering or coating layers may be used to control the release of the components. Similarly, when modified release is facilitated by the inclusion of a specific matrix material, controlling the choice and amount of modified release matrix material utilized may be used to control the release of the active components. The matrix material may be present, either surrounding individual components of the composition or over a layer of the composition, in any amount that is sufficient to yield the desired time release or time lag between release of the components.

Various coating materials that modify the release of the components in the desired manner may be used. In particular, coating materials suitable for use in the practice include, but are not limited to polymer coating materials, hydrogels and gel-forming materials and hydrophilic polymers. Preferred polymer coating materials are cellulose acetate phthalate, cellulose acetate trimaletate, hydroxypropyl methylcellulose phthalate, polyvinyl acetate phthalate, amino methacrylate copolymers such as Eudragit® RS and RL, polyacrylic acid and polyacrylate and methacrylate copolymers such as Eudragit® S and L, polyvinyl acetaldiethylamino acetate, hydroxypropyl methylcellulose acetate succinate, and shellac.

Preferred hydrogels and gel-forming materials include carboxyvinyl polymers, sodium alginate, sodium carmellose, calcium carmellose, sodium carboxymethyl starch, polyvinyl alcohol, hydroxyethyl cellulose, methyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, crosslinked starch, microcrystalline cellulose, chitin, aminoacryl-methacrylate copolymer (Eudragit® RS-PM), pullulan, collagen, casein, agar, gum arabic, sodium carboxymethyl cellulose, (swellable hydrophilic polymers) poly(hydroxyalkyl methacrylate) (molecular weight about 5 k-5,000 k), polyvinylpyrrolidone (molecular weight about 10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene pectin (molecular weight about 30 k-300 k), polysaccharides such as agar, acacia, karaya, tragacanth, algins and guar, polyacrylamides, Polyox® polyethylene oxides (molecular weight about 100 k-5,000 k), AquaKeep® acrylate polymers, diesters of polyglucan, crosslinked polyvinyl alcohol and poly N-vinyl-2-pyrrolidone, and sodium starch glycolate (e.g., Explotab®).

Preferred hydrophilic polymers include polysaccharides, methyl cellulose, sodium or calcium carboxymethyl cellulose, hydroxypropyl methyl cellulose, hydroxypropyl cellulose, hydroxyethyl cellulose, nitrocellulose, carboxymethyl cellulose, cellulose ethers, polyethylene oxides (e.g. Polyox®, Union Carbide), methylethyl cellulose, ethylhydroxy ethylcellulose, cellulose acetate, cellulose butyrate, cellulose propionate, gelatin, collagen, starch, maltodextrin, pullulan, polyvinylpyrrolidone, polyvinyl alcohol, polyvinyl acetate, glycerol fatty acid esters, polyacrylamide, polyacrylic acid, copolymers of methacrylic acid or methacrylic acid (e.g., Eudragit®), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof.

Excipients such as plasticisers, lubricants, solvents and the like may be added to a coating. Suitable plasticisers include for example hydroxylated soy lecithin, acetylated monoglycerides, butyl phthalyl butyl glycolate, dibutyl tartrate, diethyl phthalate, dimethyl phthalate, ethyl phthalyl ethyl glycolate, glycerin, propylene glycol, triacetin, citrate, tripropioin, diacetin, dibutyl phthalate, acetyl monoglyceride, polyethylene glycols, castor oil, triethyl citrate, polyhydric alcohols, glycerol, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

A coating layer may be any suitable modified release matrix material or suitable combination of modified release matrix materials. Such materials are known to those skilled in the art. Modified release matrix materials suitable for the practice of the present invention include, but are not limited to, microcrystalline cellulose, sodium carboxymethylcellulose, hydroxyalkylcelluloses (e.g., hydroxypropylmethylcellulose and hydroxypropylcellulose), polyethylene oxide, alkylcelluloses (e.g., methylcellulose and ethylcellulose), polyethylene glycol, polyvinylpyrrolidone, cellulose acetate, cellulose acetate butyrate, cellulose acetate phthalate, cellulose acetate trimellitate, polyvinylacetate phthalate, polyalkylmethacrylates, polyvinyl acetate and mixtures thereof.

The dissolution characteristics of a dosage form can be manipulated not only through the quantity of the excipients in the finished dosage form and size of the finished dosage form, but also by a judicious selection and blending of various molecular weights of a given polymer or polymers, as is known to those skilled in the art.

Film coated tablets may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, to mask an obnoxious odor or taste, or to improve to usual properties of an unsightly uncoated tablet. Compressed tablets, for example, without limitation, may be prepared by mixing the components with excipients intended to add binding or disintegration qualities. The mixture is either directly compressed, or granulated then compressed, using methods and machinery quite well known to those in the industry.

One or more of the dosage units of the nutritional supplement system described herein can also be used to deliver prebiotics. Example prebiotics include oligosaccharides such as glucose, fructose, xylose, galactose, lactose, mannose, arabinose, D-fucose, L-fucose, rhamnose, Actilight, Biotose, Palatinose, IMO, cellobiose, gentiobiose, laevan, maltodextrin, maltose, melibiose, raffinose, lactose, panorich, melezitose, raftiline, raftilose, stachyose, sucrose, tagatose, xylan, fructooligosaccharide (FOS), galactooligosaccharide (GOS), soy oligosaccharide, lactosucrose, maltooligosaccharide, xylooligosaccharide, inulin and fractionated inulin as well as one or more dietary fiber components such as coconut (including coconut endosperm fibber), beet pulp (such as sugarbeet pulp), chicory (including chicory pulp), oat bran concentrate, rice bran, carob bean, gum talhar and guar gum.

The nutritional supplement system will be better understood with reference to the following specific discussion and examples which detail certain procedures for the preparation of the dosage units. All references made to specific examples are for the purposes of illustration. They are not to be considered limiting as to the scope and nature of the present invention.

First Dosage Unit

The first dosage unit is formulated to contain vitamins and minerals, typically at or near their USFDA Daily Value (DV) level, that best are delivered in the stomach. Such nutrients include vitamins, minerals and other dietary supplement ingredients that benefit from release in the stomach and exposure to stomach acid, or that are not adversely affected by such release or exposure, and/or that properly are dispersed in the stomach for optimal absorption further down the GI tract.

This dosage unit advantageously is in the form of a tablet or caplet formed by compression of a blend containing vitamins, minerals and appropriate excipients. Because rapid delivery of nutrients is desired, the first dosage unit should be formulated for release in less than one hour, and best within 0.75 hour.

The tablet or caplet may be coated with a layer containing one or more nutrients that best are delivered particularly rapidly. Advantageously, the coating will include folic acid (folate) for rapid release. As described in U.S. Pat. Nos. 6,852,335 and 6,465,013, folic acid in an outer coating is released more rapidly than when folic acid is contained in the core of a tablet, resulting in increased bioavailability.

The first dosage unit optimally is formulated to include:
from 0 mg to 600 mg of phosphorus,
from 50 mg to 600 mg of magnesium,
from 30 mg to 500 mg of vitamin C,
from 1 mg to 30 mg of zinc,
from 30 IU to 400 IU of vitamin E,
from 0 mg to 5 mg of manganese,
from 5 mg to 50 mg of vitamin B3,
from 0 mg to 5 mg of boron,
from 0.5 mg to 5 mg of copper,
from 0 IU to 10,000 IU of vitamin A,
from 0 mg to 6 mg of beta carotene,
from 1 mg to 30 mg of pantothenic acid,
from 0 mg to 200 mcg of trace mineral protein hydrolysate for chromium, molybdenum, nickel, tin, vanadium, and selenium,
from 0 mcg to 200 mcg of vitamin K,
from 0 mg to 100 mg of N-acetyl cysteine,
from 0 mg to 25 mg of silicon,
from 1 mg to 10 mg of vitamin B6,
from 1 mg to 10 mg of vitamin B1,
from 1 mg to 10 mg of vitamin B2,
from 3 mcg to 25 mcg of vitamin B12,
from 200 IU to 800 IU of vitamin D3,
from 100 mcg to 800 mcg of folate,
from 50 mcg to 600 mcg of biotin, and
from 50 mcg to 500 mcg of iodine.

Example formulations of a first nutritional supplement dosage unit, in the form of immediate release tablets, are shown in the following table:

| Ingredient | Men's Vitamin/ Mineral Tablet Label Claim (per dose) | Women's Vitamin/ Mineral Tablet Label Claim (per dose) | Senior's Vitamin/ Mineral Tablet Label Claim (per dose) |
|---|---|---|---|
| Dicalcium phosphate (Ca) | 450 mg | 450 mg | 450 mg |
| Dicalcium phosphate (P) | 350 mg | 350 mg | 350 mg |
| Magnesium oxide | 200 mg | 200 mg | 200 mg |
| Microcrystalline cellulose | n/a | n/a | n/a |
| Ascorbic acid | 120 mg | 120 mg | 120 mg |
| Zinc gluconate | 15 mg | 15 mg | 22.5 mg |
| Ferrous fumarate | 18 mg | n/a | n/a |
| Hydroxypropyl methylcellulose | n/a | n/a | n/a |
| Vitamin E succinate | 60 IU | 60 IU | 60 IU |
| Manganese gluconate | 2 mg | 2 mg | 2 mg |
| Croscarmellose sodium | n/a | n/a | n/a |
| Niacinamide | 20 mg | 20 mg | 30 mg |
| Boron protein hydrolysate | 1 mg | 1 mg | 1 mg |
| Magnesium stearate | n/a | n/a | n/a |
| Copper gluconate | 2 mg | 2 mg | 2 mg |
| Vitamin A acetate | 2500 IU | 2500 IU | 1500 IU |
| Beta carotene | 2500 IU | 2500 IU | 1500 IU |
| d-Calcium pantothenate | 10 mg | 10 mg | 15 mg |
| Sea kelp powder | n/a | n/a | n/a |
| Selenium* | 70 mcg | 70 mcg | 70 mcg |
| Chromium* | 120 mcg | 120 mcg | 120 mcg |
| Molybdenum* | 75 mcg | 75 mcg | 75 mcg |
| Nickel* | 15 mcg | 15 mcg | 5 mcg |
| Tin* | 10 mcg | 10 mcg | 10 mcg |
| Vanadium* | 20 mcg | 20 mcg | 20 mcg |
| Vitamin K | 80 mcg | 80 mcg | 80 mcg |
| N-acetyl cysteine | n/a | n/a | 25 mg |
| Spirulina | n/a | n/a | n/a |
| Inositol | n/a | n/a | n/a |
| Choline bitartrate | n/a | n/a | n/a |
| Alfalfa powder | n/a | n/a | n/a |
| Grapefruit bioflavonoid | n/a | n/a | n/a |
| Hesperidin complex | n/a | n/a | n/a |
| Lemon bioflavonoid | n/a | n/a | n/a |
| Mixed tocopherols | n/a | n/a | n/a |
| Orange bioflavonoid | n/a | n/a | n/a |
| Rice bran powder | n/a | n/a | n/a |
| Rose hips powder | n/a | n/a | n/a |
| Acerola extract | n/a | n/a | n/a |
| Silicon dioxide | 2 mg | 2 mg | 2 mg |
| Pyridoxine hydrochloride | 2 mg | 2 mg | 4 mg |
| Thiamine mononitrate | 1.5 mg | 1.5 mg | 2.25 mg |
| Riboflavin (nutrient) | 1.7 mg | 1.7 mg | 2.55 mg |
| Riboflavin (color) | n/a | n/a | n/a |
| Hydroxylated soy lecithin | n/a | n/a | n/a |
| Carnauba wax | n/a | n/a | n/a |
| Vitamin $B_{12}$ | 6 mcg | 6 mcg | 24 mcg |
| Vitamin $D_3$ | 400 IU | 400 IU | 800 IU |
| Folic acid | 400 mcg | 400 mcg | 400 mcg |
| Biotin | 300 mcg | 300 mcg | 300 mcg |
| Potassium iodide (I) | 150 mcg | 150 mcg | 150 mcg |

*Supplied as a trace mineral protein hydrolysate

Coated tablets were assembled by combining the ingredients to form the blend for a core and compressing the blend to form tablets. The tablets were then coated with a film coating solution. Two such tablets served as one day's dose of the first dosage unit.

Second Dosage Unit

The second dosage unit is formulated to contain nutrients that do not require release in the stomach and exposure to stomach acid for efficient digestion and absorption, and which may cause tolerance problems (repeating, stomach upset, nausea) or loss in biological activity when released in the stomach. This dosage unit advantageously is used to deliver certain nutritional oils, notably fish oil constituents, other omega-3 fatty acid containing oils, and may also include fat-soluble micronutrients that do not require stomach digestion, such as vitamins A, D, E, and carotenoids.

The dosage unit advantageously is a sealed gelatin encapsulation that can pass through the stomach before releasing the encapsulated nutrients.

This dosage unit is formulated to pass through the stomach without releasing its contents, notably fish oil, and remain unopened until after it naturally passes into the intestines of the upper GI tract. Release in the stomach can lead to an unpleasant taste caused by repeating fish oil aroma ("fish burp") in the mouth of a user.

This dosage form thus advantageously is a soft capsule having a coating resistant to gastric juice to achieve a delayed release of the fish oil in the intestine, advantageously a coating of a polymer such as methacrylic acid. Delayed release can also be accomplished or enhanced by cross-linking of gelatin used to form such a capsule or by providing derivates of starch in the casing of such a capsule.

The second dosage unit optimally is formulated to include:
from 0 mg to 10 mg of lutein,
from 0 mg to 10 mg of lycopene,
from 50 IU to 400 IU of vitamin D3,
from 50 IU to 400 IU of vitamin E,
from 50 mg to 3500 mg of total omega-3 fatty acids (fish oil), and
from 0 mg to 250 mg of gamma-tocopherol.

An example formulation of a second nutritional supplement dosage unit, in the form of a soft gelatin capsule, is shown in the following table:

| Ingredient | Enteric Coated Fat Soluble Nutrients Label Claim (per dose) |
|---|---|
| Lutein ester suspension | 2 mg |
| Lycopene suspension | 2.5 mg |
| Vitamin $D_3$ | 200 IU |
| Mixed tocotrienols & tocopherols | 1 mg |
| Vitamin E (a-tocopherol concentrate) | 140 IU |
| Total omega-3 fatty acids | 500 mg |
| Gamma tocopherol | 25 mg |
| Beta and delta tocopherol | 10 mg |
| Silicon dioxide | n/a |
| Beeswax | n/a |
| Glycerin | n/a |
| Gelatin | n/a |
| Annatto suspension (Ultrabix 03190) | n/a |
| Water | n/a |
| Enteric coating (TM29Z19241 Clear) | n/a |
| Surelease (E-7-19040) | n/a |
| Natural vanillin | n/a |

The nutritional ingredients were mixed to form a fill mixture. Gel mass ingredients were mixed to form a gel mass. Formed halves were injected with the fill mixture and then joined to form capsules. Coating ingredients were mixed to make a coating mixture; and then the formed capsules were coated with the mixture in a tablet coating apparatus. The finished product was then dried.

Two of the resulting encapsulations served as one day's dose of the second dosage unit.

Third Dosage Unit

The third dosage unit is formulated to contain one or more water-soluble nutrients and/or other nutrients that are typically very rapidly absorbed and therefore best delivered by sustained release so as to maintain an elevated concentration in the body over time.

Certain rapidly-absorbed, typically water-soluble nutrients are best delivered by sustained release so as to maintain an elevated concentration in the body over time. These include B-vitamins and vitamin C. If given in an immediate release dosage unit, the concentrations of such vitamins in the body rapidly decline after an initial peak. Moreover, the absorptive sites and nutrient uptake mechanisms in the intestinal wall can be overwhelmed by the high intestinal nutrient concentrations caused by immediate release dosage units, which is known to reduce the overall amount that can be taken up by the body. Sustained release dosage units of such vitamins have been used to overcome these problems. But sustained release dosage units of such vitamins have typically excluded vitamin B12 because of the perceived need to deliver an entire dose of vitamin B12 to the stomach so that it can be combined with intrinsic factor.

Testing now shows that vitamin B12, delivered by sustained release, can result in improved bioavailability of vitamin B12 as compared to immediate release in the stomach. In the particular tests conducted, subjects were given a tablet containing 9.8 mg vitamin B1, 11.5 mg vitamin B2, 13.1 mg vitamin B6, 90 μg vitamin B12 and 518 mg vitamin C. For the B vitamins, ingestion of a comparable immediate-release formulation produced peak plasma concentrations for B1, B2 and B6 at 2 hours post ingestion and at 3 hours for serum vitamin B12. B-vitamin concentrations then declined rapidly from peak concentrations, returning to baseline by 6 hr for B1 and B6 and by 12 hr for B2 and B12. In contrast, ingestion of the sustained release formulation resulted in delayed peak serum and plasma concentrations until 4 hr for B1 and B2 and 5 hr for B6 and B12. Sustained-release tablet delivery was found to improve the bioavailability of vitamin C and at least three B-vitamins, including vitamin B12, in comparison to immediate release delivery.

The third dosage unit thus is formulated to release vitamin B12 in the stomach and intestines of the upper GI tract, advantageously in an amount that is greater than or at multiple levels of the DV (Daily Value) of vitamin B12. This is accomplished by including vitamin B12 in an amount of from 3 mcg to 500 mcg, with best results at a vitamin B12 amount of from 6 mcg to 500 mcg.

Best results for the delivery of vitamin B12 are achieved with a dosage unit that releases vitamin B12, as determined by USP dissolution apparatus at 37° C. at 50 RPM paddle speed in 900 ml of 0.1N HCl, continuously and generally linearly over a period of 6 hours. It is particularly advantageous for the dosage unit to be formulated to allow at least 15% of the vitamin B12 to dissolve in one hour in 900 ml of 0.1N HCl at 37° C. This dosage form, after ingestion by a subject, will sustain plasma levels of the vitamin B12 for a period 12 hours. Good delivery of vitamin B12 is achieved, for example, with third dosage unit tablet of 350 mg to 1500 mg total weight, where the tablet contains 20 mcg to 100 mcg of vitamin B12 and contains 5% to 20% HPMC K100/E15 by weight. Superior results are achieved with tablets having 9.5% to 14% HPMC K100/E15.

The third dosage unit also can be used to deliver one or more other water-soluble nutrients, particularly other B-vitamins and vitamin C, advantageously at or above or at multiple levels of their DVs (Daily Values) where applicable. The dosage unit thus advantageously will include 30 mg to 1000 mg of vitamin C, 1 mg to 40 mg of vitamin B1, 1 mg to 40 mg of vitamin B2, 10 mg to 300 mg of niacin, 10 mg to 300 mg of vitamin B5, and 1 mg to 40 mg of vitamin B6. A particularly useful formulation includes from 30 mg to 750 mg of vitamin C, from 25 mg to 400 mg of calcium, from 1 mg to 40 mg of vitamin B1, from 1 mg to 40 mg of vitamin B2, from 10 mg to 300 mg of vitamin B5, from 1 mg to 40 mg of vitamin B6, from 6 mcg to 500 mcg of vitamin B12, from 1 mg to 100 mg of bioflavonoid complex, and from 5 mg to 300 mg of quercetin.

The third dosage unit is designed to slowly, in a generally linear fashion, release the one or more of such water-soluble nutrients. The release of the water-soluble nutrients in general should occur in the stomach and small intestine (duodenum, jejunum and ileum).

Generally, when a supplement is taken with a meal, as commonly recommended, it takes about 6-12 hours to pass through stomach and small intestine. Therefore release of the water-soluble vitamins from the third dosage unit should extend for at least three hours after ingestion, and advantageously for up to a full twelve hours after ingestion. The third dosage unit also advantageously will be formulated to release vitamin B12 such that plasma levels of the vitamin B12 are sustained for a period of at least 6 hours, with best results achieved when formulated such that plasma levels of the vitamin B12 are sustained during the period of from 30 minutes to 24 hours after ingestion.

An example formulation of a third nutritional supplement dosage unit, in the form of a sustained release tablet, is shown in the following table:

| Ingredient | Sustained Release Vitamin B + C Tablet Label Claim (per dose) |
|---|---|
| Calcium ascorbate (Ca) | 43 mg |
| Calcium ascorbate (Vitamin C) | 380 mg |
| Calcium carbonate (Ca) | 7 mg |
| Thiamin mononitrate | 7.5 mg |
| Riboflavin | 8.5 mg |
| Niacinamide | 100 mg |
| Calcium pantothenate | 50 mg |
| Pyridoxine hydrochloride | 10 mg |
| Vitamin $B_{12}$ | 30 mcg |
| Citrus bioflavonoids | 25 mg |
| Quercetin | 50 mg |
| Microcrystalline cellulose | n/a |
| Magnesium stearate | n/a |
| Silicon dioxide | n/a |
| Hydroxypropyl methylcellulose | n/a |
| Hydroxylated soy lecithin | n/a |

Tablet contents were mixed, and tablets were formed from the resulting mixture. Coating ingredients were mixed, and the resulting mixture was used to coat the tablets.

Fourth Dosage Unit

The fourth dosage unit contains nutrients and/or other supplement ingredients, such as probiotics, that are adversely affected by exposure to stomach acid or stomach digestion and that should be delivered into the lower parts of the small intestine for full activity in the large intestine.

This dosage unit is formulated to protect the probiotic microorganisms from potentially lethal acid exposure during passage through the stomach. This can be accomplished using coated or enteric-coated tablets or capsules and other solid dosage delivery forms, where the coating is designed to deliver the ingredients into the lower intestinal tract (ileum and colon).

In one arrangement the fourth dosage unit is in the form of layered capsule as described in U.S. Pat. No. 5,478,570.

Particularly useful is a triple layer, enteric release encapsulation which protects live probiotic organisms from the acidic gastric environment and releases the organisms in the intestinal tract where they can flourish and provide their health benefits.

For the triple layer delivery system, the inner layer or core contains the probiotic organisms (preferably *Lactobacillus acidophilus* and *Bifidobacterium longum*) suspended in vegetable oil. The middle layer, composed of hardened vegetable oil, surrounds and protects the inner layer. The outer layer or primary protective shell is composed of gelatin, pectin and glycerine and provides stability from heat, freezing and acid.

The capsule has an outer shell that does not dissolve under pH 4 (at 37° C.) and thus is adapted to pass through the stomach intact. Once the capsule reaches the higher pH environment in the intestines, the outer gelatin shell begins to slowly dissolve, gradually exposing the inner lipid layers. The probiotics are then gradually released by the further action of lipolytic enzymes and the motion of the intestinal tract.

The fourth dosage unit optimally is formulated to include:
from 250,000 cfu to 20 billion cfu of *Lactobacillus acidophilus*,
and from 250,000 cfu to 20 billion cfu of *Buifodobacterium longum*.

An example formulation of a fourth nutritional supplement dosage unit, in the form of a delayed release capsule, is shown in the following table:

| Ingredient | Triple-Layer Probiotic Capsule Label Claim (per dose) |
| --- | --- |
| *Lactobacillus acidophilus* | 250M CFU |
| *Bifidobacterium longum* | 250M CFU |
| Coconut/palm oil | n/a |
| Gelatin | n/a |
| Glycerin | n/a |
| Soy lecithin | n/a |
| Pectin | n/a |

The ingredients were combined in layered capsules. A core of each capsule contained the *Lactobacillus acidophilus* and *Buifodobacterium longum*.

The core was covered by a layer of the vegetable oil to protect the beneficial bacteria during passage through the stomach. The gelatin was provided as an outer shell over the vegetable oil to provide further protection from the acidic stomach environment.

In a second example arrangement, the forth dosage unit can be formed using a sodium alginate-ethylcellulose enteric coating system for soft gelatin capsules.

In this arrangement, the composition of enteric film basically consists of sodium alginate and ethylcellulose. The sodium alginate is insoluble in acids where the pH of the resulting solution (coating solution) falls below 3.0. The ethylcellulose is insoluble in water, but it is a very good film forming and adhesive polymer while the sodium alginate is a crystalline powder which does not have filming capability.

An ethylcellulose coating solution can be formed by processing ethylcellulose in an alkaline aqueous solution (ammonia solution) to form a latex solution, for example, Surelease® coating, by Colorcon, West Point, Pa., USA. Small ethylcellulose particles (latex) are able to disperse uniformly in a solution for coating applications. By spraying the ethylcellulose latex aqueous solution on tablets in a coating system upon heating, the ammonia and water are evaporated and the ethylcellulose latexes are left on the tablet surface. Under heated condition, the latexes then can be annealed together to form a non-water soluble film on the tablet surface.

Small molecular sodium alginate can be provided in the ethylcellulose aqueous solution. The sodium alginate will dissolve in the latex alkaline solution to form an enteric coating solution. Once the enteric coating solution is sprayed on the tablets (2-4 percent solid gain), the ammonia and water are evaporated. Ethylcellulose latexes then can be annealed to form a film. The sodium alginate and ethylcellulose (sodium alginate-ethylcellulose solid solution) is molecularly mixed and uniformly coated on the tablet surface.

Once the enteric coated tablets are administered and reach stomach, the enteric coated tablets will stay intact in the acid condition (pH 2.6) for 6-12 hours. Both sodium alginate and ethylcellulose do not dissolve and will prevent water from penetrating into the core tablet to avoid premature release of the active ingredient. Once the tablets reach the intestine, the film starts to dissolve and the content of tablets are released instantly. The ratio of sodium alginate and ethylcellulose can be varied to control the release pattern and insure an instant, full release in the target physiological site for the best bioavailability.

Preferred Formulation

In its entirety, a preferred nutritional supplement system includes vitamin A, vitamin B1, vitamin B2, vitamin B3, vitamin C, vitamin D3, vitamin E, vitamin B5, vitamin B6, vitamin B12, vitamin B, vitamin K, lutein, lycopene, omega-3 fatty acids (from fish oil), gamma-tocopherol, silicon, beeswax, calcium, niacin, bioflavonoid complex, quercetin, phosphorus, magnesium, zinc, manganese, boron, copper, beta carotene, trace mineral protein hydrolysate for chromium, molybdenum, nickel, tin, vanadium, boron and selenium, N-acetyl cysteine, spirulena, folate, biotin, iodine, probiotic Acidopholis, and probiotic Bifidus.

A particularly complete and advantageous system comprises
from 0 mg to 10 mg of lutein,
from 0 mg to 10 mg of lycopene,
from 200 IU to 2000 IU of vitamin D3,
from 80 IU to 450 IU of vitamin E,
from 50 mg to 3500 mg of total omega-3 fatty acids (fish oil),
from 0 mg to 250 mg of gamma-tocopherol,
from 0 mg to 25 mg of silicon,
from 30 mg to 1000 mg of vitamin C,
from 25 mg to 1200 mg of elemental calcium, dosed in the form of a pharmaceutically acceptable calcium compound,
from 1 mg to 41 mg of vitamin B1,
from 1 mg to 41 mg of vitamin B2,
from 5 mg to 300 mg of niacin,
from 10 mg to 300 mg of vitamin B5,
from 1 mg to 40 mg of vitamin B6,
from 3 mcg to 503 mcg of vitamin B12,
from 0 mg to 100 mg of bioflavonoid complex,
from 0 mg to 300 mg of quercetin,
from 0 mg to 25 mg of silicon,
from 0 mg to 1200 mg of phosphorus,
from 50 mg to 600 mg of magnesium,
from 1 mg to 30 mg of zinc,
from 0 mg to 10 mg of manganese,
from 0 mg to 10 mg of boron,
from 0.5 mg to 5 mg of copper,
from 0 IU to 10,000 IU of vitamin A,
from 0 mg to 12 mg of beta carotene,
from 0 mg to 200 mcg of chromium, molybdenum, nickel, tin, vanadium, and selenium, from 0 mcg to 200 mcg of vitamin K,
from 0 mg to 100 mg of N-acetyl cysteine,
from 100 mcg to 1000 mcg of folate,
from 10 mcg to 600 mcg of biotin,
from 50 mcg to 500 mcg of iodine,
from 250,000 cfu to 20 billion cfu of probiotic Acidopholis, and
from 250,000 cfu to 20 billion cfu of probiotic Bifidus.

In one embodiment for women, the supplement system is additionally comprised of from 5 mg to 30 mg of iron.

In one embodiment formulated for users above the age of fifty, the supplement system is additionally comprised of 100 mcg to 1000 mcg of additional folic acid.

It will be appreciated that advantageous systems for the delivery of nutrients also can employ fewer than all four of the dosage units in some instances. A nutritional supplement delivery system, particularly well adapted for the delivery of nutrients, consists of the first, second, and third dosage units. A nutritional supplement system, particularly well adapted for the delivery of water-soluble nutrients, consists of the first and third dosage units.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

The invention claimed is:

1. A method for treating vitamin deficiency in a human subject in need thereof, the method comprising orally administering a nutritional supplement system to a human subject, a daily dose of the nutritional supplement system consisting essentially of:
   a first nutritional supplement dosage unit, the first dosage unit being in the form of at least one first dosage element formulated to release one or more nutrients in the stomach of a human subject, the one or more nutrients being selected from phosphorus, magnesium, vitamin C, zinc, vitamin E, manganese, vitamin B3, boron, copper, vitamin A, beta carotene, pantothenic acid, chromium, molybdenum, nickel, tin, vanadium, iron, selenium, vitamin K, N-acetyl cysteine, silicon, vitamin B6, vitamin B1, vitamin B2, vitamin B12, vitamin D, folate, folic acid, biotin, iodine and any combination thereof;
   a second nutritional supplement dosage unit, the second dosage unit being in the form of at least one second dosage element formulated to release one or more nutrients in the upper intestinal tract of the subject, the one or more nutrients being selected from lutein, lycopene, vitamin D3, vitamin E, omega-3 fatty acids, gamma tocopherol, beta tocopherol, delta tocopherol, and any combination thereof;
   a third nutritional supplement dosage unit, the third dosage unit being in the form of at least one third dosage element formulated to continually release one or more nutrients starting in the stomach and continuing into the upper intestinal tract of the subject, the one or more nutrients being selected from vitamin C, calcium, vitamin B1, vitamin B2, vitamin B5, vitamin B6, vitamin B12, bioflavonoid complex, quercetin, and any combination thereof; and
   a fourth nutritional supplement dosage unit, the fourth dosage unit being in the form of at least one fourth dosage element formulated to release one or more supplement ingredients in the lower intestinal tract of the subject, the supplement ingredients being selected from probiotic organisms;
   wherein each first dosage element, second dosage element, third dosage element and fourth dosage element is a tablet, a caplet or a gel encapsulation, and
   wherein the one or more nutrients of the first dosage unit, the one or more nutrients of the second dosage unit, and the one or more nutrients of the third dosage unit are different.

2. The method of claim 1 wherein:
   the first nutritional supplement dosage unit comprises a plurality of vitamins and minerals and is formulated for immediate release in the subject's stomach;
   the second nutritional supplement dosage unit comprises omega-3 fatty acids;
   the third nutritional supplement dosage unit comprises vitamin B12 and is formulated for sustained release of vitamin B12 starting in the stomach and continuing into the intestines of the subject sufficient to provide elevated plasma levels of vitamin B12 for a period 12 hours after ingestion; and
   the fourth nutritional supplement dosage unit comprises *Lactobacillus acidophilus* and *Bifidobacterium longum.*

3. The method of claim 2 wherein the third dosage unit further comprises:
   one or more additional B-vitamin(s); and
   vitamin C.

4. The method of claim 1 wherein the third nutritional supplement dosage unit comprises vitamin B12 and is formulated to provide elevated plasma levels of vitamin B12 for a period of at least 12 hours after ingestion.

5. The method of claim 1 wherein the third nutritional supplement dosage unit comprises vitamin B12 and is formulated to allow at least 15% of the vitamin B12 to dissolve in one hour in 900 ml of 0.1N HCl at 37° C.

6. The method of claim 1 wherein:
   the first nutritional supplement dosage unit consists of two tablets or two caplets;
   the second nutritional supplement dosage unit consists of two gel encapsulations;
   the third nutritional supplement dosage unit consists of one tablet or caplet; and
   the fourth nutritional supplement dosage unit consists of one layered tablet.

7. The method of claim 6 wherein the six dosage unit elements of the first, second, third, and fourth dosage units are packaged in a common blister pack such that a day's complete dose is packaged together.

8. The method of claim 1 further comprising administering the first, second, third and fourth nutritional supplement dosage units substantially simultaneously.

9. The method of claim 1 wherein:
   the first nutritional supplement dosage unit comprises:
      from 0 mg to 600 mg of phosphorus,
      from 50 mg to 600 mg of magnesium,
      from 30 mg to 500 mg of vitamin C,
      from 1 mg to 30 mg of zinc,
      from 30 IU to 400 IU of vitamin E,
      from 0 mg to 5 mg of manganese,
      from 5 mg to 50 mg of vitamin B3,
      from 0 mg to 5 mg of boron,
      from 0.5 mg to 5 mg of copper,
      from 0 IU to 10,000 IU of vitamin A,
      from 0 mg to 6 mg of beta carotene,
      from 1 mg to 30 mg of pantothenic acid,
      from 0 mg to 200 mcg of trace mineral protein hydrolysate for chromium, molybdenum, nickel, tin, vanadium, and selenium,
      from 0 mcg to about 200 mcg of vitamin K, from 0 mg to 100 mg of N-acetyl cysteine,
from 0 mg to 25 mg of silicon,
from 1 mg to 10 mg of vitamin B6,
from 1 mg to 10 mg of vitamin B1,
from 1 mg to 10 mg of vitamin B2,
from 3 mcg to 25 mcg of vitamin B12,
from 200 IU to 800 IU of vitamin D3,
from 100 mcg to 800 mcg of folate,
from 50 mcg to 600 mcg of biotin, and
from 50 mcg to 500 mcg of iodine;
the second nutritional supplement dosage unit comprises:
from 0 mg to 10 mg of lutein,
from 0 mg to 10 mg of lycopene,
from 50 IU to 400 IU of vitamin D3,
from 50 IU to 400 IU of vitamin E,
from 50 mg to 3500 mg of total omega-3 fatty acids (fish oil), and
from 0 mg to 250 mg of gamma-tocopherol;
the third nutritional supplement dosage unit comprises
from 30 mg to 750 mg of vitamin C,
from 25 mg to 400 mg of calcium,
from 1 mg to 40 mg of vitamin B1,
from 1 mg to 40 mg of vitamin B2,
from 10 mg to 300 mg of vitamin B5,
from 1 mg to 40 mg of vitamin B6,
from 6 mcg to 500 mcg of vitamin B12,
from 0 mg to 100 mg of bioflavonoid complex,
from 0 mg to 300 mg of quercetin; and
the fourth nutritional supplement dosage unit comprises:
from 250,000 cfu to 20 billion cfu of *Lactobacillus acidophilus,*
and from 250,000 cfu to 20 billion cfu of *Bifidobacterium longum.*

10. The method of claim 9 wherein the first nutritional supplement dosage unit further comprises from 5 mg to 30 mg of iron.

11. The method of claim 9 wherein the first nutritional supplement dosage unit further comprises from 100 mcg to 1000 mcg of folic acid.

12. A nutritional supplement system for human subjects, a daily dose of the nutritional supplement system consisting essentially of:
a first nutritional supplement dosage unit, the first dosage unit being in the form of at least one first dosage element formulated to release one or more nutrients in the stomach of a human subject, the one or more nutrients being selected from phosphorus, magnesium, vitamin C, zinc, vitamin E, manganese, vitamin B3, boron, copper, vitamin A, beta carotene, pantothenic acid, chromium, molybdenum, nickel, tin, vanadium, iron, selenium, vitamin K, N-acetyl cysteine, silicon, vitamin B6, vitamin B1, vitamin B2, vitamin B12, vitamin D, folate, folic acid, biotin, iodine and any combination thereof;
a second nutritional supplement dosage unit, the second dosage unit being in the form of at least one second dosage element formulated to release one or more nutrients in the upper intestinal tract of the subject, the one or more nutrients being selected from lutein, lycopene, vitamin D3, vitamin E, omega-3 fatty acids, gamma tocopherol, beta tocopherol, delta tocopherol, and any combination thereof;
a third nutritional supplement dosage unit, the third dosage unit being in the form of at least one third dosage element formulated to continually release one or more nutrients starting in the stomach and continuing into the upper intestinal tract of the subject, the one or more nutrients being selected from vitamin C, calcium, vitamin B1, vitamin B2, vitamin B5, vitamin B6, vitamin B12, bioflavonoid complex, quercetin, and any combination thereof; and
a fourth nutritional supplement dosage unit, the fourth dosage unit being in the form of at least one fourth dosage element formulated to release one or more supplement ingredients in the lower intestinal tract of the subject, the supplement ingredients being selected from probiotic organisms;
wherein each first dosage element, second dosage element, third dosage element and fourth dosage element is a tablet, a caplet or a gel encapsulation, and
wherein the one or more nutrients of the first dosage unit, the one or more nutrients of the second dosage unit, and the one or more nutrients of the third dosage unit are different.

13. The system of claim 12 wherein:
the first nutritional supplement dosage unit comprises a plurality of vitamins and minerals and is formulated for immediate release in the subject's stomach;
the second nutritional supplement dosage unit comprises nutritional oils including omega-3 fatty acids;
the third nutritional supplement dosage unit comprises vitamin B12 and is formulated for sustained release of vitamin B12 starting in the stomach and continuing into the intestines of the subject; and
the fourth nutritional supplement dosage unit comprises *Lactobacillus acidophilus* and *Bifidobacterium longum.*

14. The system of claim 13 wherein the third dosage unit further comprises:
one or more additional B-vitamin(s); and
vitamin C.

15. The system of claim 12 wherein the third nutritional supplement dosage unit comprises vitamin B12 and is formulated to provide elevated plasma levels of vitamin B12 for a period of at least 12 hours after ingestion.

16. The system of claim 12 wherein the third nutritional supplement dosage unit comprises vitamin B12 and is formulated to allow at least 15% of the vitamin B12 to dissolve in one hour in 900 ml of 0.1N HCl at 37° C.

17. The system of claim 12 wherein:
the first nutritional supplement dosage unit consists of two tablets or two caplets;
the second nutritional supplement dosage unit consists of two gel encapsulations;
the third nutritional supplement dosage unit consists of one tablet or caplet; and
the fourth nutritional supplement dosage unit consists of one layered tablet.

18. The system of claim 17 wherein the six dosage unit elements of the first, second, third, and fourth dosage units are packaged in a common blister pack such that a day's complete dose is packaged together.

19. The system of claim 12 wherein:
the first nutritional supplement dosage unit comprises:
from 0 mg to 600 mg of phosphorus,
from 50 mg to 600 mg of magnesium,
from 30 mg to 500 mg of vitamin C,
from 1 mg to 30 mg of zinc,
from 30 IU to 400 IU of vitamin E,
from 0 mg to 5 mg of manganese,
from 5 mg to 50 mg of vitamin B3,
from 0 mg to 5 mg of boron,
from 0.5 mg to 5 mg of copper,
from 0 IU to 10,000 IU of vitamin A,
from 0 mg to 6 mg of beta carotene,
from 1 mg to 30 mg of pantothenic acid, from 0 mg to 200 mcg of trace mineral protein hydrolysate for chromium, molybdenum, nickel, tin, vanadium, and selenium,
from 0 mcg to about 200 mcg of vitamin K,
from 0 mg to 100 mg of N-acetyl cysteine,
from 0 mg to 25 mg of silicon,
from 1 mg to 10 mg of vitamin B6,
from 1 mg to 10 mg of vitamin B1,
from 1 mg to 10 mg of vitamin B2,
from 3 mcg to 25 mcg of vitamin B12,
from 200 IU to 800 IU of vitamin D3,
from 100 mcg to 800 mcg of folate,
from 50 mcg to 600 mcg of biotin, and
from 50 mcg to 500 mcg of iodine;

the second nutritional supplement dosage unit comprises:
from 0 mg to 10 mg of lutein,
from 0 mg to 10 mg of lycopene,
from 50 IU to 400 IU of vitamin D3,
from 50 IU to 400 IU of vitamin E,
from 50 mg to 3500 mg of total omega-3 fatty acids (fish oil), and
from 0 mg to 250 mg of gamma-tocopherol;

the third nutritional supplement dosage unit comprises
from 30 mg to 750 mg of vitamin C,
from 25 mg to 400 mg of calcium,
from 1 mg to 40 mg of vitamin B1,
from 1 mg to 40 mg of vitamin B2,
from 10 mg to 300 mg of vitamin B5,
from 1 mg to 40 mg of vitamin B6,
from 6 mcg to 500 mcg of vitamin B12,
from 0 mg to 100 mg of bioflavonoid complex,
from 0 mg to 300 mg of quercetin; and the fourth nutritional supplement dosage unit comprises:
from 250,000 cfu to 20 billion cfu of *Lactobacillus acidophilus*,
and from 250,000 cfu to 20 billion cfu of *Bifidobacterium longum*.

20. The system of claim 19 wherein the first nutritional supplement dosage unit further comprises from 5 mg to 30 mg of iron.

21. The system of claim 19 wherein the first nutritional supplement dosage unit further comprises from 100 mcg to 1000 mcg of folic acid.

* * * * *